（12）United States Patent
Dotson et al.

(10) Patent No.: US 8,779,045 B2
(45) Date of Patent: Jul. 15, 2014

(54) THERMOPLASTIC POLYMER COMPOSITION

(75) Inventors: Darin L. Dotson, Moore, SC (US); Robbie Willem Johan M. Hanssen, Boiling Springs, SC (US); Jiannong Xu, Greer, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 12/903,686

(22) Filed: Oct. 13, 2010

(65) Prior Publication Data

US 2011/0105664 A1    May 5, 2011

Related U.S. Application Data

(63) Continuation-in-part of application No. 12/579,686, filed on Oct. 15, 2009, now abandoned.

(51) Int. Cl.
*C08K 5/098* (2006.01)
*C08K 5/00* (2006.01)
*C08L 23/02* (2006.01)
*C07C 53/134* (2006.01)

(52) U.S. Cl.
CPC .......... *C08K 5/098* (2013.01); *C08K 5/0091* (2013.01); *C08L 23/02* (2013.01); *C07C 53/134* (2013.01); *C08K 5/0083* (2013.01); *Y10S 521/908* (2013.01)
USPC .......... 524/396; 524/300; 524/301; 524/320; 524/394; 524/400; 524/543; 524/582; 524/583; 524/585; 525/333.7; 525/366; 525/386; 525/384; 521/908

(58) Field of Classification Search
USPC ............ 525/333.7, 366, 386, 384; 524/300, 524/301, 320, 394, 396, 400, 543, 582, 583, 524/585; 521/908
See application file for complete search history.

(56) References Cited

U.S. PATENT DOCUMENTS

| | | | |
|---|---|---|---|
| 2,816,883 A | | 12/1957 | Larchar et al. |
| 3,268,499 A | * | 8/1966 | Wales ............... 524/368 |
| 3,367,926 A | * | 2/1968 | Voeks ............... 524/84 |
| 4,532,280 A | * | 7/1985 | Kobayashi et al. ........ 524/108 |
| 5,049,605 A | | 9/1991 | Rekers |
| 5,891,963 A | | 4/1999 | Brookhart et al. |
| 5,919,983 A | | 7/1999 | Rosen et al. |
| 5,998,576 A | * | 12/1999 | Sadamitsu et al. ........ 530/210 |
| 6,107,230 A | | 8/2000 | McDaniel et al. |
| 6,300,271 B1 | | 10/2001 | McDaniel et al. |
| 6,632,894 B1 | | 10/2003 | McDaniel et al. |
| 6,649,558 B2 | | 11/2003 | Brown et al. |
| 7,157,510 B2 | | 1/2007 | Xie et al. |
| 7,262,236 B2 | | 8/2007 | Xie et al. |
| 2003/0194552 A1 | * | 10/2003 | Pittman et al. ........ 428/364 |
| 2007/0080485 A1 | * | 4/2007 | Kerscher et al. ........ 264/564 |

FOREIGN PATENT DOCUMENTS

| | | |
|---|---|---|
| EP | 0 475 242 A2 | 9/1991 |
| GB | 1 419 040 | 12/1975 |
| JP | 58-11533 | 1/1983 |
| WO | 2006/067073 | * 6/2006 |

OTHER PUBLICATIONS

Beck, Journal of Applied Polymer Science, vol. 11, pp. 673-685, 1967.*
White, Journal of Chemical Education, vol. 75, No. 9, Sep. 1998, p. 1119-1120.*
Database WPI, Week 198309, Thomson Scientific, London, GB; AN 1983-21260K, XP002616380, (Showa Denko KK); Jan. 22, 1983 Abstract.
International Search Report and The Written Opinion of the International Searching Authority for PCT/US2010/052588.

* cited by examiner

*Primary Examiner* — Robert C Boyle
(74) *Attorney, Agent, or Firm* — Robert M. Lanning

(57) ABSTRACT

A thermoplastic polymer composition comprises a thermoplastic polymer and a nucleating agent. The nucleating agent comprises a compound conforming to the structure of Formula (I) or Formula (II)

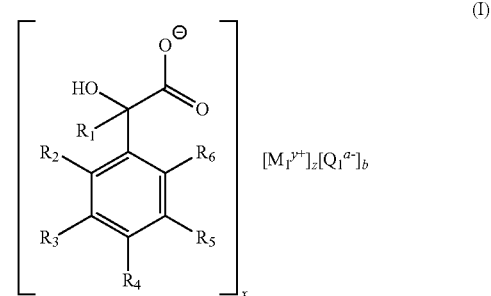

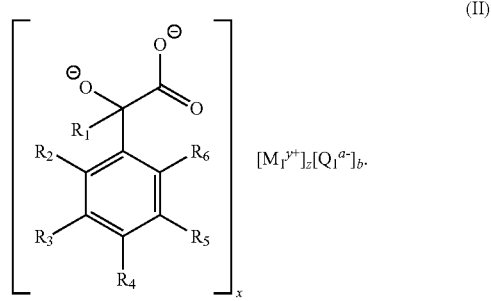

7 Claims, No Drawings

THERMOPLASTIC POLYMER COMPOSITION

CROSS-REFERENCE TO RELATED PATENT APPLICATIONS

This application is a continuation-in-part of and, pursuant to 35 U.S.C. §120, claims the benefit of the filing date of U.S. patent application Ser. No. 12/579,686 filed on Oct. 15, 2009 now abandoned.

TECHNICAL FIELD OF THE INVENTION

This application relates to nucleating agents for thermoplastic polymers, thermoplastic polymer compositions comprising such nucleating agents, articles made from such thermoplastic polymer compositions, and methods for making and molding such thermoplastic polymer compositions.

BACKGROUND OF THE INVENTION

Several nucleating agents for thermoplastic polymers are known in the art. These nucleating agents generally function by forming nuclei or providing sites for the formation and/or growth of crystals in the thermoplastic polymer as it solidifies from a molten state. The nuclei or sites provided by the nucleating agent allow the crystals to form within the cooling polymer at a higher temperature and/or at a more rapid rate than the crystals will form in the virgin, non-nucleated thermoplastic polymer. These effects can then permit processing of a nucleated thermoplastic polymer composition at cycle times that are shorter than the virgin, non-nucleated thermoplastic polymer.

While polymer nucleating agents may function in a similar manner, not all nucleating agents are created equal. For example, a particular nucleating agent may be very effective at increasing the peak polymer recrystallization temperature of a thermoplastic polymer, but the rapid rate of crystallization induced by such a nucleating agent may cause excessive and/or uneven (anisotropic) shrinkage of a molded part produced from a thermoplastic polymer composition containing the nucleating agent.

Given the complicated interrelationship of these properties and the fact that many nucleating agents exhibit less-than-optimal behavior for at least one of these properties, a need remains for nucleating agents that are capable of producing thermoplastic polymer compositions exhibiting a more desirable combination of high peak polymer crystallization temperature, low, isotropic shrinkage, and high stiffness. Applicants believe that the nucleating agents and thermoplastic polymer compositions disclosed in the present application meet such a need.

BRIEF SUMMARY OF THE INVENTION

As noted above, the present invention generally relates to nucleating agents, thermoplastic polymer compositions comprising such nucleating agents, articles (e.g., molded articles) made from such thermoplastic polymer compositions, and methods for making and molding such thermoplastic polymer compositions. The nucleating agents and thermoplastic polymer compositions according to the invention are believed to be particularly well-suited for the production of thermoplastic polymer articles (e.g., molded thermoplastic polymer articles) exhibiting a desirable combination of physical properties. In particular, articles produced using the nucleating agents and thermoplastic polymer compositions of the invention are believed to exhibit a desirable combination of a higher peak polymer recrystallization temperature and higher stiffness, as compared to articles made from the non-nucleated thermoplastic polymer. Also, when compared to articles made from thermoplastic polymer compositions containing other nucleating agents, articles produced using the nucleating agents and thermoplastic polymer compositions of the invention are believed to exhibit a desirable combination of a relatively high peak polymer recrystallization temperature, and relatively isotropic shrinkage. Applicants believe that this combination of physical properties indicates that the nucleating agents and thermoplastic polymer compositions according to the invention are well-suited for use in the production of thermoplastic polymer articles.

In a first embodiment, the invention provides a thermoplastic polymer composition comprising a thermoplastic polymer and a nucleating agent. The nucleating agent comprises a compound conforming to the structure of Formula (I) or Formula (II)

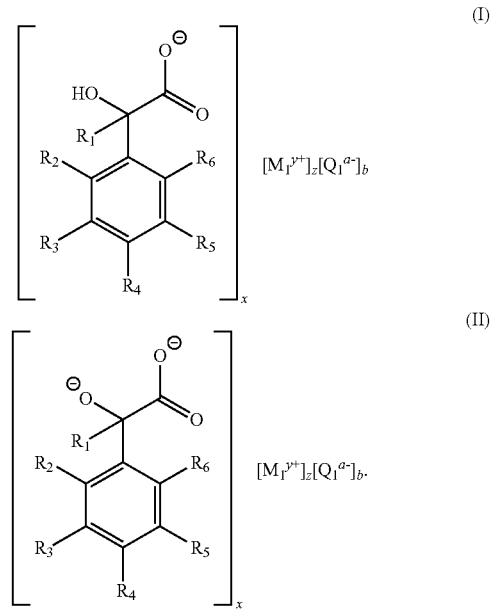

In each of the structures of Formula (I) and Formula (II), x is a positive integer; and $R_1$, $R_2$, $R_3$, $R_4$, $R_5$, and $R_6$ are substituents independently selected from the group consisting of hydrogen, hydroxyl, $C_1$-$C_9$ alkyl groups, $C_1$-$C_9$ alkenyl groups, $C_1$-$C_9$ alkynyl groups, $C_1$-$C_{15}$ alkoxy groups, $C_1$-$C_9$ hydroxyalkyl groups, alkyl ether groups, amine groups, $C_1$-$C_9$ alkylamine groups, halogens, aryl groups, alkylaryl groups, and geminal or vicinal carbocyclic groups having up to nine carbon atoms. Each $M_1$ is a metal cation, y is the valence of the metal cation, and z is a positive integer. The variable b can be zero or any positive integer. If b is one or greater, each $Q_1$ is a negatively-charged counterion, and a is the valence of the counterion. When the compound conforms to the structure of Formula (I), the values of x, y, z, a, and b satisfy the equation x+(ab)=yz; and when the compound conforms to the structure of Formula (II), the values of x, y, z, a, and b satisfy the equation 2x+(ab)=yz.

The invention also provides methods for making such a thermoplastic polymer composition and methods for using the thermoplastic polymer composition to form thermoplastic polymer articles.

DETAILED DESCRIPTION OF THE INVENTION

In a first embodiment, the invention provides a thermoplastic polymer composition comprising a thermoplastic polymer and a nucleating agent. The thermoplastic polymer of the thermoplastic polymer composition can be any suitable thermoplastic polymer. As utilized herein, the term "thermoplastic polymer" is used to refer to a polymeric material that will melt upon exposure to sufficient heat to form a flowable liquid and will return to a solidified state upon sufficient cooling. In their solidified state, such thermoplastic polymers exhibit either crystalline or semi-crystalline morphology. Suitable thermoplastic polymers include, but are not limited to, polyolefins (e.g., polyethylenes, polypropylenes, polybutylenes, and any combinations thereof), polyamides (e.g., nylon), polyurethanes, polyesters (e.g., polyethylene terephthalate), and the like, as well as any combinations thereof.

In certain embodiments, the thermoplastic polymer can be a polyolefin, such as a polypropylene, a polyethylene, a polybutylene, and a poly(4-methyl-1-pentene). In a possibly preferred embodiment, the thermoplastic polymer is a polyolefin selected from the group consisting of polypropylene homopolymers (e.g., atactic polypropylene, isotactic polypropylene, and syndiotactic polypropylene), polypropylene copolymers (e.g., polypropylene random copolymers), polypropylene impact copolymers, polyethylene, polyethylene copolymers, polybutylene, poly(4-methyl-1-pentene), and mixtures thereof. Suitable polypropylene copolymers include, but are not limited to, random copolymers made from the polymerization of propylene in the presence of a comonomer selected from the group consisting of ethylene, but-1-ene (i.e., 1-butene), and hex-1-ene (i.e., 1-hexene). In such polypropylene random copolymers, the comonomer can be present in any suitable amount, but typically is present in an amount of less than about 10 wt. % (e.g., about 1 to about 7 wt. %). Suitable polypropylene impact copolymers include, but are not limited to, those produced by the addition of a copolymer selected from the group consisting of ethylene-propylene rubber (EPR), ethylenepropylene-diene monomer (EPDM), polyethylene, and plastomers to a polypropylene homopolymer or polypropylene random copolymer. In such polypropylene impact copolymers, the copolymer can be present in any suitable amount, but typically is present in an amount of from about 5 to about 25 wt. %.

In another possibly preferred embodiment, the thermoplastic polymer can be a polyethylene. Suitable polyethylenes include, but are not limited to, low density polyethylene, linear low density polyethylene, medium density polyethylene, high density polyethylene, and combinations thereof. In certain possibly preferred embodiments, the thermoplastic polymer is selected from the group consisting of medium density polyethylene, high density polyethylene, and mixtures thereof. In another possibly preferred embodiment, the thermoplastic polymer is a high density polyethylene.

The high density polyethylene polymers suitable for use in the invention generally have a density of greater than about 0.940 g/cm$^3$. There is no upper limit to the suitable density of the polymer, but high density polyethylene polymers typically have a density that is less than about 0.980 g/cm$^3$ (e.g., less than about 0.975 g/cm$^3$).

The high density polyethylene polymers suitable for use in the invention can be either homopolymers or copolymers of ethylene with one or more α-olefins. Suitable α-olefins include, but are not limited to, 1-butene, 1-hexene, 1-octene, 1-decene, and 4-methyl-1-pentene. The comonomer can be present in the copolymer in any suitable amount, such as an amount of about 5% by weight or less (e.g., about 3 mol. % or less). As will be understood by those of ordinary skill in the art, the amount of comonomer suitable for the copolymer is largely driven by the end use for the copolymer and the required or desired polymer properties dictated by that end use.

The high density polyethylene polymers suitable for use in the invention can be produced by any suitable process. For example, the polymers can be produced by a free radical process using very high pressures as described, for example, in U.S. Pat. No. 2,816,883 (Larchar et al.), but the polymers typically are produced in a "low pressure" catalytic process. In this context, the term "low pressure" is used to denote processes carried out at pressures less than 6.9 MPa (e.g., 1,000 psig), such as 1.4-6.9 MPa (200-1,000 psig). Examples of suitable low pressure catalytic processes include, but are not limited to, solution polymerization processes (i.e., processes in which the polymerization is performed using a solvent for the polymer), slurry polymerization processes (i.e., processes in which the polymerization is performed using a hydrocarbon liquid in which the polymer does not dissolve or swell), gas-phase polymerization processes (e.g., processes in which the polymerization is performed without the use of a liquid medium or diluent), or a staged reactor polymerization process. The suitable gas-phase polymerization processes also include the so-called "condensed mode" or "super-condensed mode" processes in which a liquid hydrocarbon is introduced into the fluidized-bed to increase the absorption of the heat producing during the polymerization process. In these condensed mode and super-condensed mode processes, the liquid hydrocarbon typically is condensed in the recycle stream and reused in the reactor. The staged reactor processes can utilize a combination of slurry process reactors (tanks or loops) that are connected in series, parallel, or a combination of series or parallel so that the catalyst (e.g., chromium catalyst) is exposed to more than one set of reaction conditions. Staged reactor processes can also be carried out by combining two loops in series, combining one or more tanks and loops in series, using multiple gas-phase reactors in series, or a loop-gas phase arrangement. Because of their ability to expose the catalyst to different sets of reactor conditions, staged reactor processes are often used to produce multimodal polymers, such as those discussed below. Suitable processes also include those in which utilize a pre-polymerization step is performed. In this pre-polymerization step, the catalyst typically is exposed to the cocatalyst and ethylene under mild conditions in a smaller, separate reactor, and the polymerization reaction is allowed to proceed until the catalyst comprises a relatively small amount (e.g., about 5% to about 30% of the total weight) of the resulting composition. This pre-polymerized catalyst is then introduced to the large-scale reactor in which the polymerization is to be performed.

The high density polyethylene polymers suitable for use in the invention can be produced using any suitable catalyst or combination of catalysts. Suitable catalysts include transition metal catalysts, such as supported reduced molybdenum oxide, cobalt molybdate on alumina, chromium oxide, and transition metal halides. Chromium oxide catalysts typically are produced by impregnating a chromium compound onto a porous, high surface area oxide carrier, such as silica, and then calcining it in dry air at 500-900° C. This converts the chromium into a hexavalent surface chromate ester or dichromate ester. The chromium oxide catalysts can be used in conjunction with metal alkyl cocatalysts, such as alkyl boron, alkyl aluminum, alkyl zinc, and alkyl lithium. Supports for the chromium oxide include silica, silica-titania, silica-alumina, alumina, and aluminophosphates. Further examples of chromium oxide catalysts include those catalysts produced by depositing a lower valent organochromium compound, such as bis(arene) $Cr^0$, allyl $Cr^{2+}$ and $Cr^{3+}$, beta stabilized alkyls of $Cr^{2+}$ and $Cr^{4+}$, and bis(cyclopentadienyl) $Cr^{2+}$, onto a chromium oxide catalyst, such as those described above. Suitable transition metal catalysts also include supported chromium catalysts such as those based on chromocene or a silylchromate (e.g., bi(trisphenylsilyl)chromate). These chromium catalysts can be supported on any suitable high surface area support such as those described above for the chromium oxide catalysts, with silica typically being used. The supported chromium catalysts can also be used in conjunction with cocatalysts, such as the metal alkyl cocatalysts listed above for the chromium oxide catalysts. Suitable transition metal halide catalysts include titanium (III) halides (e.g., titanium (III) chloride), titanium (IV) halides (e.g., titanium (IV) chloride), vanadium halides, zirconium halides, and combinations thereof. These transition metal halides are often supported on a high surface area solid, such as magnesium chloride. The transition metal halide catalysts are typically used in conjunction with an aluminum alkyl cocatalyst, such as trimethylaluminum (i.e., $Al(CH_3)_3$) or triethylaluminum (i.e., $Al(C_2H_5)_3$). These transition metal halides may also be used in staged reactor processes. Suitable catalysts also include metallocene catalysts, such as cyclopentadienyl titanium halides (e.g., cyclopentadienyl titanium chlorides), cyclopentadienyl zirconium halides (e.g., cyclopentadienyl zirconium chlorides), cyclopentadienyl hafnium halides (e.g., cyclopentadienyl hafnium chlorides), and combinations thereof. Metallocene catalysts based on transition metals complexed with indenyl or fluorenyl ligands are also known and can be used to produce high density polyethylene polymers suitable for use in the invention. The catalysts typically contain multiple ligands, and the ligands can be substituted with various groups (e.g., n-butyl group) or linked with bridging groups, such as $—CH_2CH_2—$ or $>SiPh_2$. The metallocene catalysts typically are used in conjunction with a cocatalyst, such as methyl aluminoxane (i.e., $(Al(CH_3)_xO_y)_n$. Other cocatalysts include those described in U.S. Pat. No. 5,919,983 (Rosen et al.), U.S. Pat. No. 6,107,230 (McDaniel et al.), U.S. Pat. No. 6,632,894 (McDaniel et al.), and U.S. Pat. No. 6,300,271 (McDaniel et al). Other "single site" catalysts suitable for use in producing high density polyethylene include diimine complexes, such as those described in U.S. Pat. No. 5,891,963 (Brookhart et al.).

The high density polyethylene polymers suitable for use in the invention can have any suitable molecular weight (e.g., weight average molecular weight). For example, the weight average molecular weight of the high density polyethylene can be from 20,000 g/mol to about 1,000,000 g/mol or more. As will be understood by those of ordinary skill in the art, the suitable weight average molecular weight of the high density polyethylene will depend, at least in part, on the particular application or end use for which the polymer is destined. For example, a high density polyethylene polymer intended for blow molding applications can have a weight average molecular weight of about 100,000 g/mol to about 1,000,000 g/mol. A high density polyethylene polymer intended for pipe applications or film applications can have a weight average molecular weight of about 100,000 g/mol to about 500,000 g/mol. A high density polyethylene polymer intended for injection molding applications can have a weight average molecular weight of about 20,000 g/mol to about 80,000 g/mol. A high density polyethylene polymer intended for wire insulation applications, cable insulation applications, tape applications, or filament applications can have a weight average molecular weight of about 80,000 g/mol to about 400,000 g/mol. A high density polyethylene polymer intended for rotomolding applications can have a weight average molecular weight of about 50,000 g/mol to about 150,000 g/mol.

The high density polyethylene polymers suitable for use in the invention can also have any suitable polydispersity, which is defined as the value obtained by dividing the weight average molecular weight of the polymer by the number average molecular weight of the polymer. For example, the high density polyethylene polymer can have a polydispersity of greater than 2 to about 100. As understood by those skilled in the art, the polydispersity of the polymer is heavily influenced by the catalyst system used to produce the polymer, with the metallocene and other "single site" catalysts generally producing polymers with relatively low polydispersity and narrow molecular weight distributions and the other transition metal catalysts (e.g., chromium catalysts) producing polymer with higher polydispersity and broader molecular weight distributions. The high density polyethylene polymers suitable for use in the invention can also have a multimodal (e.g., bimodal) molecular weight distribution. For example, the polymer can have a first fraction having a relatively low molecular weight and a second fraction having a relatively high molecular weight. The difference between the weight average molecular weight of the fractions in the polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight.

The high density polyethylene polymers suitable for use in the invention can have any suitable melt index. For example, the high density polyethylene polymer can have a melt index of about 0.01 dg/min to about 40 dg/min. As with the weight average molecular weight, those of ordinary skill in the art understand that the suitable melt index for the high density polyethylene polymer will depend, at least in part, on the particular application or end use for which the polymer is destined. Thus, for example, a high density polyethylene polymer intended for blow molding applications can have a melt index of about 0.01 dg/min to about 1 dg/min. A high density polyethylene polymer intended for pipe applications or film applications can have a melt index of about 0.02 dg/min to about 0.8 dg/min. A high density polyethylene polymer intended for injection molding applications can have a melt index of about 2 dg/min to about 80 dg/min. A high density polyethylene polymer intended for rotomolding applications can have a melt index of about 0.5 dg/min to about 10 dg/min. A high density polyethylene polymer intended for tape applications can have a melt index of about 0.2 dg/min to about 4 dg/min. A high density polyethylene polymer intended for filament applications can have a melt index of about 1 dg/min to about 20 dg/min. The melt index of the polymer is measured using ASTM Standard D1238-04c.

The high density polyethylene polymers suitable for use in the invention generally do not contain high amounts of long-chain branching. The term "long-chain branching" is used to refer to branches that are attached to the polymer chain and are of sufficient length to affect the rheology of the polymer (e.g., branches of about 130 carbons or more in length). If desired for the application in which the polymer is to be used, the high density polyethylene polymer can contain small amounts of long-chain branching. However, the high density polyethylene polymers suitable for use in the invention typically contain very little long-chain branching (e.g., less than about 1 long-chain branch per 10,000 carbons, less than about 0.5 long-chain branches per 10,000 carbons, less than about 0.1 long-chain branches per 10,000 carbons, or less than about 0.01 long-chain branches per 10,000 carbons).

The medium density polyethylene polymers suitable for use in the invention generally have a density of about 0.926 g/cm$^3$ to about 0.940 g/cm$^3$. The term "medium density polyethylene" is used to refer to polymers of ethylene that have a density between that of high density polyethylene and linear low density polyethylene and contain relatively short branches, at least as compared to the long branches present in low density polyethylene polymers produced by the free radical polymerization of ethylene at high pressures.

The medium density polyethylene polymers suitable for use in the invention generally are copolymers of ethylene and at least one α-olefin, such as 1-butene, 1-hexene, 1-octene, 1-decene, and 4-methyl-1-pentene. The α-olefin comonomer can be present in any suitable amount, but typically is present in an amount of less than about 8% by weight (e.g., less than about 5 mol %). As will be understood by those of ordinary skill in the art, the amount of comonomer suitable for the copolymer is largely driven by the end use for the copolymer and the required or desired polymer properties dictated by that end use.

The medium density polyethylene polymers suitable for use in the invention can be produced by any suitable process. Like the high density polyethylene polymers, the medium density polyethylene polymers typically are produced in "low pressure" catalytic processes such as any of the processes described above in connection with the high density polyethylene polymers suitable for use in the invention. Examples of suitable processes include, but are not limited to, gas-phase polymerization processes, solution polymerization processes, slurry polymerization processes, and staged reactor processes. Suitable staged reactor processes can incorporate any suitable combination of the gas-phase, solution, and slurry polymerization processes described above. As with high density polyethylene polymers, staged reactor processes are often used to produce multimodal polymers.

The medium density polyethylene polymers suitable for use in the invention can be produced using any suitable catalyst or combination of catalysts. For example, the polymers can be produced using Ziegler catalysts, such as transition metal (e.g., titanium) halides or esters used in combination with organoaluminum compounds (e.g., triethylaluminum). These Ziegler catalysts can be supported on, for example, magnesium chloride, silica, alumina, or magnesium oxide. The medium density polyethylene polymers suitable for use in the invention can also be produced using so-called "dual Ziegler catalysts," which contain one catalyst species for dimerizing ethylene into 1-butene (e.g., a combination of a titanium ester and triethylaluminum) and another catalyst for copolymerization of ethylene and the generated 1-butene (e.g., titanium chloride supported on magnesium chloride).

The medium density polyethylene polymers suitable for use in the invention can also be produced using chromium oxide catalysts, such as those produced by depositing a chromium compound onto a silica-titania support, oxidizing the resulting catalyst in a mixture of oxygen and air, and then reducing the catalyst with carbon monoxide. These chromium oxide catalysts typically are used in conjunction with cocatalysts such as trialkylboron or trialkylaluminum compounds. The chromium oxide catalysts can also be used in conjunction with a Ziegler catalyst, such as a titanium halide- or titanium ester-based catalyst. The medium density polyethylene polymers suitable for use in the invention can also be produced using supported chromium catalysts such as those described above in the discussion of catalysts suitable for making high density polyethylene. The medium density polyethylene polymers suitable for use in the invention can also be produced using metallocene catalysts. Several different types of metallocene catalysts can be used. For example, the metallocene catalyst can contain a bis(metallocene) complex of zirconium, titanium, or hafnium with two cyclopentadienyl rings and methylaluminoxane. As with the catalysts used in high density polyethylene production, the ligands can be substituted with various groups (e.g., n-butyl group) or linked with bridging groups. Another class of metallocene catalysts that can be used are composed of bis(metallocene) complexes of zirconium or titanium and anions of perfluorinated boron-aromatic compounds. A third class of metallocene catalysts that can be used are referred to as constrained-geometry catalysts and contain monocyclopentadienyl derivatives of titanium or zirconium in which one of the carbon atoms in the cyclopentadienyl ring is linked to the metal atom by a bridging group. These complexes are activated by reacting them with methylaluminoxane or by forming ionic complexes with noncoordinative anions, such as $B(C_6F_5)_4^-$ or $B(C_6F_5)_3CH_3^-$. A fourth class of metallocene catalysts that can be used are metallocene-based complexes of a transition metal, such as titanium, containing one cyclopentadienyl ligand in combination with another ligand, such as a phosphinimine or —O—SiR$_3$. This class of metallocene catalyst is also activated with methylaluminoxane or a boron compound. Other catalysts suitable for use in making the linear low density polyethylene suitable for use in the invention include, but are not limited to, the catalysts disclosed in U.S. Pat. No. 6,649,558.

The medium density polyethylene polymers suitable for use in the invention can have any suitable compositional uniformity, which is a term used to describe the uniformity of the branching in the copolymer molecules of the polymer. Many commercially-available medium density polyethylene polymers have a relatively low compositional uniformity in which the high molecular weight fraction of the polymer contains relatively little of the α-olefin comonomer and has relatively little branching while the low molecular weight fraction of the polymer contains a relatively high amount of the α-olefin comonomer and has a relatively large amount of branching. Alternatively, another set of medium density polyethylene polymers have a relatively low compositional uniformity in which the high molecular weight fraction of the polymer contains a relatively high amount of the α-olefin comonomer while the low molecular weight fraction of the polymer contains relatively little of the α-olefin comonomer. The compositional uniformity of the polymer can be measured using any suitable method, such as temperature rising elution fractionation.

The medium density polyethylene polymers suitable for use in the invention can have any suitable molecular weight. For example, the polymer can have a weight average molecular weight of about 50,000 g/mol to about 200,000 g/mol. As will be understood by those of ordinary skill in the art, the suitable weight average molecular weight of the medium density polyethylene will depend, at least in part, on the particular application or end use for which the polymer is destined.

The medium density polyethylene polymers suitable for use in the invention can also have any suitable polydispersity. Many commercially available medium density polyethylene polymers have a polydispersity of about 2 to about 30. The medium density polyethylene polymers suitable for use in the invention can also have a multimodal (e.g., bimodal) molecular weight distribution. For example, the polymer can have a first fraction having a relatively low molecular weight and a second fraction having a relatively high molecular weight. As with the high density polyethylene polymers suitable for use in the invention, the difference between the weight average molecular weight of the fractions in the multimodal medium density polyethylene polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight The medium density polyethylene polymers suitable for use in the invention can have any suitable melt index. For example, the medium density polyethylene polymer can have a melt index of about 0.01 dg/min to about 200 dg/min. As with the weight average molecular weight, those of ordinary skill in the art understand that the suitable melt index for the medium density polyethylene polymer will depend, at least in part, on the particular application or end use for which the polymer is destined. Thus, for example, a medium density polyethylene polymer intended for blow molding applications or pipe applications can have a melt index of about 0.01 dg/min to about 1 dg/min. A medium density polyethylene polymer intended for film applications can have a melt index of about 0.5 dg/min to about 3 dg/min. A medium density polyethylene polymer intended for injection molding applications can have a melt index of about 6 dg/min to about 200 dg/min. A medium density polyethylene polymer intended for rotomolding applications can have a melt index of about 4 dg/min to about 7 dg/min. A medium density polyethylene polymer intended for wire and cable insulation applications can have a melt index of about 0.5 dg/min to about 3 dg/min. The melt index of the polymer is measured using ASTM Standard D1238-04c.

The medium density polyethylene polymers suitable for use in the invention generally do not contain a significant amount of long-chain branching. For example, the medium density polyethylene polymers suitable for use in the invention generally contain less than about 0.1 long-chain branches per 10,000 carbon atoms (e.g., less than about 0.002 long-chain branches per 100 ethylene units) or less than about 0.01 long-chain branches per 10,000 carbon atoms.

The linear low density polyethylene polymers suitable for use in the invention generally have a density of 0.925 g/cm$^3$ or less (e.g., about 0.910 g/cm$^3$ to about 0.925 g/cm$^3$). The term "linear low density polyethylene" is used to refer to lower density polymers of ethylene having relatively short branches, at least as compared to the long branches present in low density polyethylene polymers produced by the free radical polymerization of ethylene at high pressures.

The linear low density polyethylene polymers suitable for use in the invention generally are copolymers of ethylene and at least one α-olefin, such as 1-butene, 1-hexene, 1-octene, 1-decene, and 4-methyl-1-pentene. The α-olefin comonomer can be present in any suitable amount, but typically is present in an amount of less than about 6 mol. % (e.g., about 2 mol % to about 5 mol %). As will be understood by those of ordinary skill in the art, the amount of comonomer suitable for the copolymer is largely driven by the end use for the copolymer and the required or desired polymer properties dictated by that end use.

The linear low density polyethylene polymers suitable for use in the invention can be produced by any suitable process. Like the high density polyethylene polymers, the linear low density polyethylene polymers typically are produced in "low pressure" catalytic processes such as any of the processes described above in connection with the high density polyethylene polymers suitable for use in the invention. Suitable processes include, but are not limited to, gas-phase polymerization processes, solution polymerization processes, slurry polymerization processes, and staged reactor processes. Suitable staged reactor processes can incorporate any suitable combination of the gas-phase, solution, and slurry polymerization processes described above. As with high density polyethylene polymers, staged reactor processes are often used to produce multimodal polymers.

The linear low density polyethylene polymers suitable for use in the invention can be produced using any suitable catalyst or combination of catalysts. For example, the polymers can be produced using Ziegler catalysts, such as transition metal (e.g., titanium) halides or esters used in combination with organoaluminum compounds (e.g., triethylaluminum). These Ziegler catalysts can be supported on, for example, magnesium chloride, silica, alumina, or magnesium oxide. The linear low density polyethylene polymers suitable for use in the invention can also be produced using so-called "dual Ziegler catalysts," which contain one catalyst species for dimerizing ethylene into 1-butene (e.g., a combination of a titanium ester and triethylaluminum) and another catalyst for copolymerization of ethylene and the generated 1-butene (e.g., titanium chloride supported on magnesium chloride). The linear low density polyethylene polymers suitable for use in the invention can also be produced using chromium oxide catalysts, such as those produced by depositing a chromium compound onto a silica-titania support, oxidizing the resulting catalyst in a mixture of oxygen and air, and then reducing the catalyst with carbon monoxide. These chromium oxide catalysts typically are used in conjunction with cocatalysts such as trialkylboron or trialkylaluminum compounds. The chromium oxide catalysts can also be used in conjunction with a Ziegler catalyst, such as a titanium halide- or titanium ester-based catalyst. The linear low density polyethylene polymers suitable for use in the invention can also be produced using supported chromium catalysts such as those described above in the discussion of catalysts suitable for making high density polyethylene. The linear low density polyethylene suitable for use in the invention can also be produced using metallocene catalysts. Several different types of metallocene catalysts can be used. For example, the metallocene catalyst can contain a bis(metallocene) complex of zirconium, titanium, or hafnium with two cyclopentadienyl rings and methylaluminoxane. As with the catalysts used in high density polyethylene production, the ligands can be substituted with various groups (e.g., n-butyl group) or linked with bridging groups. Another class of metallocene catalysts that can be used are composed of bis(metallocene) complexes of zirconium or titanium and anions of perfluorinated boronaromatic compounds. A third class of metallocene catalysts that can be used are referred to as constrained-geometry catalysts and contain monocyclopentadienyl derivatives of titanium or zirconium in which one of the carbon atoms in the cyclopentadienyl ring is linked to the metal atom by a bridging group. These complexes are activated by reacting them with methylaluminoxane or by forming ionic complexes with noncoordinative anions, such as $B(C_6F_5)_4^-$ or $B(C_6F_5)_3CH_3^-$. A fourth class of metallocene catalysts that can be used are metallocene-based complexes of a transition metal, such as titanium, containing one cyclopentadienyl ligand in combination with another ligand, such as a phosphinimine or —O—$SiR_3$. This class of metallocene catalyst is also activated with methylaluminoxane or a boron compound. Other catalysts suitable for use in making the linear low density polyethylene suitable for use in the invention include, but are not limited to, the catalysts disclosed in U.S. Pat. No. 6,649,558.

The linear low density polyethylene polymers suitable for use in the invention can have any suitable compositional uniformity, which is a term used to describe the uniformity of the branching in the copolymer molecules of the polymer. Many commercially-available linear low density polyethylene polymers have a relatively low compositional uniformity in which the high molecular weight fraction of the polymer contains relatively little of the α-olefin comonomer and has relatively little branching while the low molecular weight fraction of the polymer contains a relatively high amount of the α-olefin comonomer and has a relatively large amount of branching. Alternatively, another set of linear low density polyethylene polymers have a relatively low compositional uniformity in which the high molecular weight fraction of the polymer contains a relatively high amount of the α-olefin comonomer while the low molecular weight fraction of the polymer contains relatively little of the α-olefin comonomer. The compositional uniformity of the polymer can be measured using any suitable method, such as temperature rising elution fractionation.

The linear low density polyethylene polymers suitable for use in the invention can have any suitable molecular weight. For example, the polymer can have a weight average molecular weight of about 20,000 g/mol to about 250,000 g/mol. As will be understood by those of ordinary skill in the art, the suitable weight average molecular weight of the linear low density polyethylene will depend, at least in part, on the particular application or end use for which the polymer is destined.

The linear low density polyethylene polymers suitable for use in the invention can also have any suitable polydispersity. Many commercially available linear low density polyethylene polymers have a relatively narrow molecular weight distribution and thus a relatively low polydispersity, such as about 2 to about 5 (e.g., about 2.5 to about 4.5 or about 3.5 to about 4.5). The linear low density polyethylene polymers suitable for use in the invention can also have a multimodal (e.g., bimodal) molecular weight distribution. For example, the polymer can have a first fraction having a relatively low molecular weight and a second fraction having a relatively high molecular weight. As with the high density polyethylene polymers suitable for use in the invention, the difference between the weight average molecular weight of the fractions in the multimodal linear low density polyethylene polymer can be any suitable amount. In fact, it is not necessary for the difference between the weight average molecular weights to be large enough that two distinct molecular weight fractions can be resolved using gel permeation chromatography (GPC). However, in certain multimodal polymers, the difference between the weight average molecular weights of the fractions can be great enough that two or more distinct peaks can be resolved from the GPC curve for the polymer. In this context, the term "distinct" does not necessarily mean that the portions of the GPC curve corresponding to each fraction do not overlap, but is merely meant to indicate that a distinct peak for each fraction can be resolved from the GPC curve for the polymer. The multimodal polymers suitable for use in the invention can be produced using any suitable process. As noted above, the multimodal polymers can be produced using staged reactor processes. One suitable example would be a staged solution process incorporating a series of stirred tanks. Alternatively, the multimodal polymers can be produced in a single reactor using a combination of catalysts each of which is designed to produce a polymer having a different weight average molecular weight The linear low density polyethylene polymers suitable for use in the invention can have any suitable melt index. For example, the linear low density polyethylene polymer can have a melt index of about 0.01 dg/min to about 200 dg/min. As with the weight average molecular weight, those of ordinary skill in the art understand that the suitable melt index for the linear low density polyethylene polymer will depend, at least in part, on the particular application or end use for which the polymer is destined. Thus, for example, a linear low density polyethylene polymer intended for blow molding applications or pipe applications can have a melt index of about 0.01 dg/min to about 1 dg/min. A linear low density polyethylene polymer intended for film applications can have a melt index of about 0.5 dg/min to about 3 dg/min. A linear low density polyethylene polymer intended for injection molding applications can have a melt index of about 6 dg/min to about 200 dg/min. A linear low density polyethylene polymer intended for rotomolding applications can have a melt index of about 4 dg/min to about 7 dg/min. A linear low density polyethylene polymer intended for wire and cable insulation applications can have a melt index of about 0.5 dg/min to about 3 dg/min. The melt index of the polymer is measured using ASTM Standard D1238-04c.

The linear low density polyethylene polymers suitable for use in the invention generally do not contain a significant amount of long-chain branching. For example, the linear low density polyethylene polymers suitable for use in the invention generally contain less than about 0.1 long-chain branches per 10,000 carbon atoms (e.g., less than about 0.002 long-chain branches per 100 ethylene units) or less than about 0.01 long-chain branches per 10,000 carbon atoms.

The low density polyethylene polymers suitable for use in the invention generally have a density of less than 0.935 g/cm$^3$ and, in contrast to high density polyethylene, medium density polyethylene and linear low density polyethylene, have a relatively large amount of long-chain branching in the polymer.

The low density polyethylene polymers suitable for use in the invention can be either ethylene homopolymers or copolymers of ethylene and a polar comonomer. Suitable polar comonomers include, but are not limited to, vinyl acetate, methyl acrylate, ethyl acrylate, and acrylic acid. These comonomers can be present in any suitable amount, with comonomer contents as high as 20% by weight being used for certain applications. As will be understood by those skilled in the art, the amount of comonomer suitable for the polymer is largely driven by the end use for the polymer and the required or desired polymer properties dictated by that end use.

The low density polyethylene polymers suitable for use in the invention can be produced using any suitable process, but typically the polymers are produced by the free-radical initiated polymerization of ethylene at high pressure (e.g., about 81 to about 276 MPa) and high temperature (e.g., about 130 to about 330° C.). Any suitable free radical initiator can be used in such processes, with peroxides and oxygen being the most common. The free-radical polymerization mechanism gives rise to short-chain branching in the polymer and also to the relatively high degree of long-chain branching that distinguishes low density polyethylene from other ethylene polymers (e.g., high density polyethylene and linear low density polyethylene). The polymerization reaction typically is performed in an autoclave reactor (e.g., a stirred autoclave reactor), a tubular reactor, or a combination of such reactors positioned in series.

The low density polyethylene polymers suitable for use in the invention can have any suitable molecular weight. For example, the polymer can have a weight average molecular weight of about 30,000 g/mol to about 500,000 g/mol. As will be understood by those of ordinary skill in the art, the suitable weight average molecular weight of the low density polyethylene will depend, at least in part, on the particular application or end use for which the polymer is destined. For example, a low density polyethylene polymer intended for blow molding applications can have a weight average molecular weight of about 80,000 g/mol to about 200,000 g/mol. A low density polyethylene polymer intended for pipe applications can have a weight average molecular weight of about 80,000 g/mol to about 200,000 g/mol. A low density polyethylene polymer intended for injection molding applications can have a weight average molecular weight of about 30,000 g/mol to about 80,000 g/mol. A low density polyethylene polymer intended for film applications can have a weight average molecular weight of about 60,000 g/mol to about 500,000 g/mol.

The low density polyethylene polymers suitable for use in the invention can have any suitable melt index. For example, the low density polyethylene polymer can have a melt index of about 0.2 to about 100 dg/min. As noted above, the melt index of the polymer is measured using ASTM Standard D1238-04c.

As noted above, one of the major distinctions between low density polyethylene and other ethylene polymers is a relatively high degree of long-chain branching within the polymer. The low density polyethylene polymers suitable for use in the invention can exhibit any suitable amount of long-chain branching, such as about 0.01 or more long-chain branches per 10,000 carbon atoms, about 0.1 or more long-chain branches per 10,000 carbon atoms, about 0.5 or more long-chain branches per 10,000 carbon atoms, about 1 or more long-chain branches per 10,000 carbon atoms, or about 4 or more long-chain branches per 10,000 carbon atoms. While there is not a strict limit on the maximum extent of long-chain branching that can be present in the low density polyethylene polymers suitable for use in the invention, the long-chain branching in many low density polyethylene polymers is less than about 100 long-chain branches per 10,000 carbon atoms.

The thermoplastic polymer composition also comprises a nucleating agent. As utilized herein, the term "nucleating agent" is used to refer to compounds or additives that form nuclei or provide sites for the formation and/or growth of crystals in a polymer as it solidifies from a molten state. The nucleating agent comprises a compound conforming to the structure of Formula (I) or Formula (II)

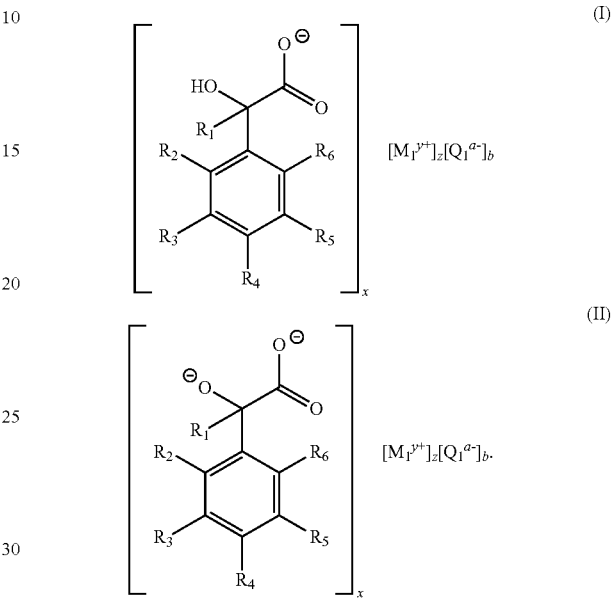

In each of the structures of Formula (I) and Formula (II), x is a positive integer; and $R_1$, $R_2$, $R_3$, $R_4$, $R_5$, and $R_6$ are substituents independently selected from the group consisting of hydrogen, hydroxyl, $C_1$-$C_9$ alkyl groups, $C_1$-$C_9$ alkenyl groups, $C_1$-$C_9$ alkynyl groups, $C_1$-$C_{15}$ alkoxy groups, $C_1$-$C_9$ hydroxyalkyl groups, alkyl ether groups, amine groups, $C_1$-$C_9$ alkylamine groups, halogens, aryl groups, alkylaryl groups, and geminal or vicinal carbocyclic groups having up to nine carbon atoms. Each $M_1$ is a metal cation, y is the valence of the metal cation, and z is a positive integer. The variable b can be zero or any positive integer. If b is one or greater, each $Q_1$ is a negatively-charged counterion, and a is the valence of the counterion. When the compound conforms to the structure of Formula (I), the values of x, y, z, a, and b satisfy the equation $x+(ab)=yz$; and when the compound conforms to the structure of Formula (II), the values of x, y, z, a, and b satisfy the equation $2x+(ab)=yz$. In certain possibly preferred embodiments, the compound conforms to the structure of Formula (I).

As noted above, $R_1$, $R_2$, $R_3$, $R_4$, $R_5$, and $R_6$ of Formula (I) and Formula (II) are substituents independently selected from the group consisting of hydrogen, hydroxyl, $C_1$-$C_9$ alkyl groups, $C_1$-$C_9$ alkenyl groups, $C_1$-$C_9$ alkynyl groups, $C_1$-$C_{15}$ alkoxy groups, $C_1$-$C_9$ hydroxyalkyl groups, alkyl ether groups, amine groups, $C_1$-$C_9$ alkylamine groups, halogens, aryl groups, alkylaryl groups, and geminal or vicinal carbocyclic groups having up to nine carbon atoms. In certain possibly preferred embodiments, $R_1$, $R_2$, $R_3$, $R_4$, $R_5$, and $R_6$ are each hydrogen. In certain other possibly preferred embodiments, $R_1$ is a phenyl group, and $R_2$, $R_3$, $R_4$, $R_5$, and $R_6$ are each hydrogen. In another possibly preferred embodiment, $R_1$ is hydrogen, one of $R_2$, $R_3$, $R_4$, $R_5$, and $R_6$ is a $C_1$-$C_{15}$ alkoxy group, and the remainder of $R_2$, $R_3$, $R_4$, $R_5$, and $R_6$ are each hydrogen.

As noted above, $M_1$ is a metal cation. Suitable metal cations include, but are not limited to, alkali metal cations (e.g., sodium), alkaline earth metal cations (e.g., calcium), transition metal cations (e.g., zinc), and group 13 metal cations (e.g., aluminum). As utilized herein, the term "transition metal" is used to refer those elements in the d-block of the periodic table of elements, which corresponds to groups 3 to 12 on the periodic table of elements. In certain possibly preferred embodiments, $M_1$ is a metal cation selected from the group consisting of calcium and zinc. In those embodiments in which the compound contains more than one metal cation $M_1$, such as an embodiment in which the compound conforms to the structure of Formula (II) and the metal cations have a valence of +1, each $M_1$ can be the same or different.

In the structures of Formulae (I) and (II), $O_1$ can represent a negatively-charged counterion. The negatively-charged counterion can be any suitable anion including, but not limited to, halides (e.g., chloride), hydroxide, and oxide anions.

In certain specific and possibly preferred embodiments of the thermoplastic polymer composition of the invention, $R_1$, $R_2$, $R_3$, $R_4$, $R_5$, and $R_6$ are each hydrogen, and $M_1$ is calcium. In such an embodiment, the thermoplastic polymer can be either a polypropylene or a polyethylene, including any of the polypropylenes and polyethylenes mentioned above. In another specific and possibly preferred embodiment of the thermoplastic polymer composition of the invention, $R_1$, $R_2$, $R_3$, $R_4$, $R_5$, and $R_6$ are each hydrogen, and $M_1$ is zinc. In such an embodiment, the thermoplastic polymer can be either a polypropylene or a polyethylene, including any of the polypropylenes and polyethylenes mentioned above. In another specific and possibly preferred embodiment of the thermoplastic polymer composition of the invention, $R_1$ is a phenyl group, $R_2$, $R_3$, $R_4$, $R_5$, and $R_6$ are each hydrogen, and $M_1$ is a metal cation selected from the group consisting of calcium and zinc. In such an embodiment, the thermoplastic polymer can be either a polypropylene or a polyethylene, including any of the polypropylenes and polyethylenes mentioned above. In another specific and possibly preferred embodiment of the thermoplastic polymer composition of the invention, $R_1$ is hydrogen, one of $R_2$, $R_3$, $R_4$, $R_5$, and $R_6$ is a $C_1$-$C_{15}$ alkoxy group, the remainder of $R_2$, $R_3$, $R_4$, $R_5$, and $R_6$ are each hydrogen, and $M_1$ is a metal cation selected from the group consisting of calcium and zinc. In such an embodiment, the thermoplastic polymer can be either a polypropylene or a polyethylene, including any of the polypropylenes and polyethylenes mentioned above.

As will be understood by those of ordinary skill in the art, the compounds conforming to the structures of Formula (I) and Formula (II) can, depending upon the substitution at $R_1$ and at $R_2$-$R_6$ on the aromatic ring, contain a stereogenic center and take the form of one of two enantiomers, the R-enantiomer or the S-enantiomer. While the compounds can contain a stereogenic center, the structures of Formulae (I) and (II) set forth above and in the appended claims do not specify or require any particular absolute configuration at such stereogenic center and, unless otherwise explicitly stated or illustrated, are intended to encompass any enantiomer having the specified substituents, regardless of its absolute configuration. When the compound contains such a stereogenic center, the nucleating agent can comprise an enantiomerically pure compound (i.e., the molecules of the compound are all one enantiomer), or the nucleating agent can comprise any suitable mixture of the two enantiomers. In certain embodiments, the nucleating agent can contain a compound that is a racemate, containing equal amounts of the R- and S-enantiomers.

The metal salt compounds of Formulae (I) and (II) can be synthesized using any suitable technique, many of which will be readily apparent to those of ordinary skill in the art. For example, if the acid(s) (e.g., mandelic acid or mandelic acid derivative) used in making the compound is commercially available, the compound can be prepared by reacting the acid with a suitable base (e.g., a base comprising the desired metal cation and a Lowry-Brønsted base) in a suitable medium (e.g., an aqueous medium). If the acid(s) to be used in making the metal salt are not commercially available, the acid(s) can be synthesized, for example, by first reacting the appropriate benzaldehyde compound (i.e., a benzaldehyde compound having the desired substitution pattern on the aromatic ring) with sodium bisulfite to produce the sodium salt of hydroxy (phenyl)methanesulfonic acid. The sodium salt of hydroxy (phenyl)methanesulfonic acid is then reacted with sodium cyanide to produce mandelonitrile (i.e., hydroxy(phenyl)acetonitrile), which is then hydrolyzed in an acidic aqueous environment to produce the desired acid. Once the desired acid is obtained, the compound can be produced as described above (e.g., by reacting the acid with a suitable base in an appropriate medium).

The nucleating agent can be present in the thermoplastic polymer composition in any suitable amount. The nucleating agent can be present in the thermoplastic polymer composition in an amount of about 50 parts per million (ppm) or more, about 100 ppm or more, about 250 ppm or more, or about 500 ppm or more, based on the total weight of the thermoplastic polymer composition. The nucleating agent typically is present in the thermoplastic polymer composition in an amount of about 10,000 ppm or less, about 7,500 ppm or less, about 5,000 ppm or less, or about 4,000 ppm or less, based on the total weight of the thermoplastic polymer composition. Thus, in certain embodiments of the thermoplastic polymer composition, the nucleating agent is present in the thermoplastic polymer composition in an amount of about 50 to about 10,000 ppm, about 100 to about 7,500 ppm (e.g., about 100 to about 5,000 ppm), about 250 ppm to about 5,000 ppm (e.g., about 250 ppm to about 4,000 ppm), or about 500 ppm to about 5,000 ppm (e.g., about 500 to about 4,000 ppm), based on the total weight of the polymer composition.

The thermoplastic polymer composition of the invention can also be provided in the form of a masterbatch composition designed for addition or let-down into a virgin thermoplastic polymer. In such an embodiment, the thermoplastic polymer composition will generally contain a higher amount of the nucleating agent as compared to a thermoplastic polymer composition intended for use in the formation of an article of manufacture without further dilution or addition to a virgin thermoplastic polymer. For example, the nucleating agent can be present in such a thermoplastic polymer composition in an amount of about 1 wt. % to about 10 wt. % (e.g., about 1 wt. % to about 5 wt. % or about 2 wt. % to about 4 wt. %), based on the total weight of the thermoplastic polymer composition.

The thermoplastic polymer composition of the invention can contain other polymer additives in addition to the aforementioned nucleating agent. Suitable additional polymer additives include, but are not limited to, antioxidants (e.g., phenolic antioxidants, phosphite antioxidants, and combinations thereof), anti-blocking agents (e.g., amorphous silica and diatomaceous earth), pigments (e.g., organic pigments and inorganic pigments) and other colorants (e.g., dyes and polymeric colorants), fillers and reinforcing agents (e.g., glass, glass fibers, talc, calcium carbonate, and magnesium oxysulfate whiskers), nucleating agents, clarifying agents, acid scavengers (e.g., metal salts of fatty acids, such as the metal salts of stearic acid), polymer processing additives (e.g., fluoropolymer polymer processing additives), polymer cross-linking agents, slip agents (e.g., fatty acid amide compounds derived from the reaction between a fatty acid and ammonia or an amine-containing compound), fatty acid ester compounds (e.g., fatty acid ester compounds derived from the reaction between a fatty acid and a hydroxyl-containing compound, such as glycerol, diglycerol, and combinations thereof), and combinations of the foregoing.

As noted above, the thermoplastic polymer composition of the invention can contain other nucleating agents in addition to those compounds conforming to the structure of Formula (I) or Formula (II). Suitable nucleating agents include, but are not limited to, 2,2'-methylene-bis-(4,6-di-tert-butylphenyl) phosphate salts (e.g., sodium 2,2'-methylene-bis-(4,6-di-tert-butylphenyl)phosphate or aluminum 2,2'-methylene-bis-(4,6-di-tert-butylphenyl)phosphate), bicyclo[2.2.1]heptane-2,3-dicarboxylate salts (e.g., disodium bicyclo[2.2.1]heptane-2,3-dicarboxylate or calcium bicyclo[2.2.1]heptane-2,3-dicarboxylate), cyclohexane-1,2-dicarboxylate salts (e.g., calcium cyclohexane-1,2-dicarboxylate, monobasic aluminum cyclohexane-1,2-dicarboxylate, dilithium cyclohexane-1,2-dicarboxylate, or strontium cyclohexane-1,2-dicarboxylate), and combinations thereof. For the bicyclo[2.2.1] heptane-2,3-dicarboxylate salts and the cyclohexane-1,2-dicarboxylate salts, the carboxylate moieties can be arranged in either the cis- or trans-configuration, with the cis-configuration being preferred.

As noted above, the thermoplastic polymer composition of the invention can also contain a clarifying agent. Suitable clarifying agents include, but are not limited to, trisamides and acetal compounds that are the condensation product of a polyhydric alcohol and an aromatic aldehyde. Suitable trisamide clarifying agents include, but are not limited to, amide derivatives of benzene-1,3,5-tricarboxylic acid, derivatives of N-(3,5-bis-formylamino-phenyl)-formamide (e.g., N-[3,5-bis-(2,2-dimethyl-propionylamino)-phenyl]-2,2-dimethyl-propionamide), derivatives of 2-carbamoyl-malonamide (e.g., N,N'-bis-(2-methyl-cyclohexyl)-2-(2-methyl-cyclohexylcarbamoyl)-malonamide), and combinations thereof. As noted above, the clarifying agent can be an acetal compound that is the condensation product of a polyhydric alcohol and an aromatic aldehyde. Suitable polyhydric alcohols include acyclic polyols such as xylitol and sorbitol, as well as acyclic deoxy polyols (e.g., 1,2,3-trideoxynonitol or 1,2,3-trideoxynon-1-enitol). Suitable aromatic aldehydes typically contain a single aldehyde group with the remaining positions on the aromatic ring being either unsubstituted or substituted. Accordingly, suitable aromatic aldehydes include benzaldehyde and substituted benzaldehydes (e.g., 3,4-dimethyl-benzaldehyde or 4-propyl-benzaldehyde). The acetal compound produced by the aforementioned reaction can be a mono-acetal, di-acetal, or tri-acetal compound (i.e., a compound containing one, two, or three acetal groups, respectively), with the di-acetal compounds being preferred. Suitable acetal-based clarifying agents include, but are not limited to, the clarifying agents disclosed in U.S. Pat. Nos. 5,049,605; 7,157,510; and 7,262,236.

The thermoplastic polymer composition of the invention can be produced by any suitable method or process. For example, the thermoplastic polymer composition can be produced by simple mixing of the individual components of the thermoplastic polymer composition (e.g., thermoplastic polymer, nucleating agent, and other additives, if any). The thermoplastic polymer composition can also be produced by mixing the individual components under high shear or high intensity mixing conditions. The thermoplastic polymer composition of the invention can be provided in any form suitable for use in further processing to produce an article of manufacture from the thermoplastic polymer composition. For example, the thermoplastic polymer compositions can be provided in the form of a powder (e.g., free-flowing powder), flake, pellet, prill, tablet, agglomerate, and the like.

The thermoplastic polymer composition of the invention is believed to be useful in producing thermoplastic polymer articles of manufacture. The thermoplastic polymer composition of the invention can be formed into a desired thermoplastic polymer article of manufacture by any suitable technique, such as injection molding (e.g., multicomponent molding, overmolding, or 2K molding), injection rotational molding, blow molding (e.g., extrusion blow molding, injection blow molding, or injection stretch blow molding), extrusion (e.g., sheet extrusion, film extrusion, cast film extrusion, pipe extrusion, or foam extrusion), thermoforming, rotomolding, film blowing (blown film), film casting (cast film), and the like. Thermoplastic polymer articles made using the thermoplastic polymer composition of the invention can be comprised of multiple layers (e.g., multilayer blown or cast films or multilayer injection molded articles), with one or any suitable number of the multiple layers containing a thermoplastic polymer composition of the invention.

The thermoplastic polymer composition of the invention can be used to produce any suitable article of manufacture. Suitable articles of manufacture include, but are not limited to, medical devices (e.g., pre-filled syringes for retort applications, intravenous supply containers, and blood collection apparatus), food packaging, liquid containers (e.g., containers for drinks, medications, personal care compositions, shampoos, and the like), apparel cases, microwavable articles, shelving, cabinet doors, mechanical parts, automobile parts, sheets, pipes, tubes, rotationally molded parts, blow molded parts, films, fibers, and the like.

The following examples further illustrate the subject matter described above but, of course, should not be construed as in any way limiting the scope thereof.

EXAMPLE 1

This example demonstrates the production of a compound conforming to the structure of Formula (I), which is suitable for use as a nucleating agent in accordance with the invention. Approximately 100 grams (0.66 mol) of DL-mandelic acid (i.e., (±)-hydroxy(phenyl)acetic acid) was added to a beaker containing approximately 400 mL of distilled water. Then, approximately 105 grams of a 50% (w/w) aqueous sodium hydroxide solution (1.32 mol) was added to the beaker. The resulting mixture was stirred for approximately 30 minutes. The water was removed from the mixture using a rotary evaporator. The resulting solid product, which was determined to be sodium mandelate, was then dried in an oven overnight at a temperature of approximately 110° C. The solid was ground to a powder suitable for use as a nucleating agent for thermoplastics.

EXAMPLE 2

This example demonstrates the production of a compound conforming to the structure of Formula (I), which is suitable for use as a nucleating agent in accordance with the invention. Approximately 100 grams (0.66 mol) of DL-mandelic acid was added to a beaker containing approximately 800 mL of distilled water. In a separate container, approximately 26.3 g (0.66 mol) of sodium hydroxide was dissolved in approximately 200 mL of distilled water. The resulting sodium hydroxide solution was then added to the beaker containing the mandelic acid, and the resulting mixture was stirred until all of the solids dissolved. Next, approximately 48.4 g (0.33 mol) of calcium chloride dihydrate was added to the resulting solution, and the mixture was stirred for approximately 30 minutes. While the mixture was being stirred, a precipitate formed. The precipitate was collected from the mixture via filtration, and the collected solids were washed three times using distilled water. The collected solid, which was determined to be calcium mandelate, was then dried in an oven overnight at a temperature of approximately 110° C. The solid was ground to a powder suitable for use as a nucleating agent for thermoplastics.

EXAMPLE 3

This example demonstrates the production of a compound conforming to the structure of Formula (I), which is suitable for use as a nucleating agent in accordance with the invention. Approximately 20 g (0.11 mol) of sodium mandelate was added to a beaker containing approximately 200 mL of distilled water. Next, approximately 14.9 g (0.11 mol) of zinc chloride was added to the beaker containing the sodium mandelate, and the resulting mixture was stirred for approximately 30 minutes. While the mixture was being stirred, a precipitate formed. The precipitate was collected from the mixture via filtration, and the collected solids were washed three times using distilled water. The collected solid, which was determined to be zinc mandelate, was then dried in an oven overnight at a temperature of approximately 110° C. The solid was ground to a powder suitable for use as a nucleating agent for thermoplastics.

EXAMPLE 4

This example demonstrates the production of a compound conforming to the structure of Formula (I), which is suitable for use as a nucleating agent in accordance with the invention. Approximately 20 g (0.11 mol) of sodium mandelate was added to a beaker containing approximately 200 mL of distilled water. Next, approximately 13.2 g (0.11 mol) of magnesium sulfate was added to the beaker containing the sodium mandelate, and the resulting mixture was stirred for approximately 30 minutes. While the mixture was being stirred, a precipitate formed. The collected solid, which was determined to be magnesium mandelate, was then dried in an oven overnight at a temperature of approximately 110° C. The solid was ground to a powder suitable for use as a nucleating agent for thermoplastics.

EXAMPLE 5

This example demonstrates the production of a compound conforming to the structure of Formula (I), which is suitable for use as a nucleating agent in accordance with the invention. Approximately 20 g (0.11 mol) of sodium mandelate was added to a beaker containing approximately 200 mL of distilled water. Next, approximately 22.6 g (0.066 mol) of aluminum sulfate was added to the beaker containing the sodium mandelate, and the resulting mixture was stirred for approximately 30 minutes. While the mixture was being stirred, a precipitate formed. The collected solid, which was determined to be aluminum mandelate, was then dried in an oven overnight at a temperature of approximately 110° C. The solid was ground to a powder suitable for use as a nucleating agent for thermoplastics.

EXAMPLE 6

This example demonstrates the production of a compound conforming to the structure of Formula (I), which is suitable for use as a nucleating agent in accordance with the invention. Approximately 9.1 g (0.05 mol) of DL-4-methoxymandelic acid (i.e., (±)-hydroxy(4-methoxyphenyl)acetic acid) and approximately 1.9 g (0.025 mol) of calcium hydroxide were added to a beaker containing approximately 100 mL of deionized water. The resulting solution was stirred for approximately 30 minutes, and the water was then removed using a rotary evaporator. The resulting solid, which was determined to be calcium 4-methoxymandelate (i.e., calcium hydroxy(4-methoxyphenyl)acetate), was then collected and dried in an oven overnight at a temperature of approximately 110° C. The solid was ground to a powder suitable for use as a nucleating agent for thermoplastics.

EXAMPLE 7

This example demonstrates the production of a compound conforming to the structure of Formula (I), which is suitable for use as a nucleating agent in accordance with the invention. Approximately 15.2 g (0.1 mol) of DL-mandelic acid, approximately 8.1 g (0.1 mol) of zinc oxide, and approximately 0.9 g (0.005 mol) of zinc acetate were added to a 500 mL 3-neck flask containing approximately 150 mL of tetrahydrofuran. The resulting mixture was then heated at reflux for approximately 7 hours. The reaction mixture was then filtered while hot, and the collected solid was washed three times with isopropyl alcohol. The resulting solid, which was determined to be zinc mandelate, was then dried in an oven overnight at a temperature of approximately 110° C. The solid was ground to a powder suitable for use as a nucleating agent for thermoplastics.

EXAMPLE 8

This example demonstrates the production of a compound conforming to the structure of Formula (I), which is suitable for use as a nucleating agent in accordance with the invention. Approximately 22.8 g (0.1 mol) of benzilic acid (i.e., hydroxy(diphenyl)acetic acid) and approximately 4.0 g (0.1 mol) of sodium hydroxide were added to a beaker containing approximately 200 mL of distilled water. The resulting solution was stirred for approximately 30 minutes, and the water was then removed using a rotary evaporator. The resulting solid, which was determined to be sodium benzilate, was then collected and dried in an oven overnight at a temperature of approximately 110° C. The solid was ground to a powder suitable for use as a nucleating agent for thermoplastics.

EXAMPLE 9

This example demonstrates the production of a compound conforming to the structure of Formula (I), which is suitable for use as a nucleating agent in accordance with the invention. Approximately 22.8 g (0.1 mol) of benzilic acid and approximately 3.7 g (0.05 mol) of calcium hydroxide were added to a beaker containing approximately 200 mL of distilled water. The resulting solution was stirred for approximately 30 minutes, and the water was then removed using a rotary evaporator. The resulting solid, which was determined to be calcium benzilate, was then collected and dried in an oven overnight at a temperature of approximately 110° C. The solid was ground to a powder suitable for use as a nucleating agent for thermoplastics.

EXAMPLE 10

This example demonstrates the production of a compound conforming to the structure of Formula (I), which is suitable for use as a nucleating agent in accordance with the invention. Approximately 22.8 g (0.1 mol) of benzilic acid and approximately 4.0 g (0.1 mol) of sodium hydroxide were added to a beaker containing approximately 200 mL of distilled water. The resulting solution was stirred for approximately 30 minutes. Next, approximately 6.8 g (0.05 mol) of zinc chloride was added to the beaker, and the resulting mixture was stirred for approximately 30 more minutes. While the mixture was being stirred, a precipitate formed. The precipitate was collected from the mixture via filtration, and the collected solids were washed three times using distilled water. The collected solid, which was determined to be zinc benzilate, was then dried in an oven overnight at a temperature of approximately 110° C. The solid was ground to a powder suitable for use as a nucleating agent for thermoplastics.

EXAMPLE 11

This example demonstrates the production of thermoplastic polymer compositions according to the invention and the nucleating capabilities of certain metal salts of mandelic acid and mandelic acid derivatives. The metal salts produced in Examples 1-10 were separately combined with a high density polyethylene polymer to produce fourteen thermoplastic polymer compositions according to the invention (i.e., Samples 11A-11N). The high density polyethylene polymer had a density of approximately 0.952 g/cm$^3$ and a melt flow index of 19 g/10 min, as measured in accordance with ASTM Standard D1238-04c using a 2.16 kg weight. A comparative thermoplastic polymer composition (Comparative Sample 1) was produced by using the high density polyethylene polymer alone (i.e., without any nucleating agent). Another comparative thermoplastic polymer composition (Comparative Sample 2) was produced by combining calcium cis-hexahydrophthalate (CaHHPA) with the same high density polyethylene polymer. The amount of nucleating agent (i.e., metal salt) contained in each sample is noted in Table 1 below.

For those compositions that were tested for shrinkage and/or flexural modulus, the thermoplastic polymer composition was produced by first combining the polyethylene polymer and the nucleating agent in a powdered form and then mixing the two for at least approximately 5 minutes using a KitchenAid® stand mixer. The resulting mixture was then melt extruded on a single screw extruder to produce a pelletized thermoplastic polymer composition. Each pelletized thermoplastic polymer composition was then formed into a part suitable for physical testing via injection molding or compression molding. The parts formed from the thermoplastic polymer compositions were then subjected to the tests described below.

For those compositions that were tested only for peak polymer recrystallization temperature (i.e., Samples 11F, 11L, 11M, and 11N), the thermoplastic polymer composition was produced by first combining ground polyethylene polymer with the nucleating agent and then mixing the two for approximately two minutes in a high intensity mixer. The resulting mixture was then extruded into a cast film on a Randcastle extruder. The resulting cast film had an average thickness of approximately 35 μm.

The peak polymer recrystallization temperature ($T_c$) for the thermoplastic polymer compositions was measured using a differential scanning calorimeter (Mettler-Toledo DSC822 differential scanning calorimeter). In particular, a sample was taken from the target part and heated at a rate of 20° C./minute from a temperature of 60° C. to 220° C., held at 220° C. for two minutes, and cooled at a rate of approximately 10° C./minute to a temperature of 60° C. The temperature at which peak polymer crystal reformation occurred (which corresponds to the peak polymer recrystallization temperature) was recorded for each sample and is reported in Table 1 below.

The flexural properties for the parts were measured in the machine direction (MD) in accordance with ASTM Standard D790. The flexural modulus for the tested parts is reported as the 1% secant modulus in Table 1 below.

The shrinkage measurements for the parts reported in Table 1 were measured in accordance with ISO Standard 294-4. The isotropy (Isot.) reported in Table 1 is reported as the product obtained by taking the shrinkage exhibited by the part in the flow direction (MD) and dividing it by the shrinkage exhibited by the part in the across the flow direction (the transverse direction or TD).

TABLE 1

Select physical properties of parts produced using Samples 11A-11N, Comparative Sample 1 (C. S. 1), and Comparative Sample 2 (C. S. 2).

| Sample | Nucleating Agent Type | Loading (ppm) | $T_c$ (° C.) | Shrinkage (Isot.) | Flexural Modulus (MPa) |
|---|---|---|---|---|---|
| C. S. 1 | — | — | 116.3 | 1.06 | 760 |
| 11A | Ex. 1 | 1,000 | — | — | 897 |
| 11B | Ex. 2 | 1,000 | 118.6 | 1.34 | 925 |
| 11C | Ex. 3 | 500 | — | — | 775 |
| 11D | Ex. 3 | 1,000 | — | 0.87 | 904 |
| 11E | Ex. 3 | 2,000 | 119.5 | — | 991 |
| 11F | Ex. 4 | 2,000 | 118.5 | — | — |
| 11G | Ex. 5 | 1,000 | — | — | 903 |
| 11H | Ex. 6 | 1,000 | 117.8 | 1.22 | 811 |
| 11I | Ex. 7 | 500 | 117.8 | 0.92 | 885 |
| 11J | Ex. 7 | 1,000 | 118.1 | 0.83 | 896 |
| 11K | Ex. 7 | 2,000 | 118.8 | 0.83 | 902 |
| 11L | Ex. 8 | 1,000 | 116.5 | — | — |
| 11M | Ex. 9 | 1,000 | 117.4 | — | — |
| 11N | Ex. 10 | 1,000 | 117.1 | — | — |
| C. S. 2 | CaHHPA | 1,000 | 118.8 | 2.11 | 902 |

As can be seen from the data set forth in Table 1, the thermoplastic polymer compositions according to the invention generally exhibit higher peak polymer recrystallization temperatures and higher flexural moduli than the virgin polymer (C.S. 1). As will be understood by those of skill in the art, higher peak polymer recrystallization temperatures typically enable the use of shorter cycle times in molding operations due to the fact that the polymer does not need to be cooled as much before it can be removed from the mold without deformation.

The data set forth in the table also suggests that, while Comparative Sample 2 exhibits a higher peak polymer recrystallization temperature than some of the thermoplastic polymer compositions according to the invention, the thermoplastic polymer compositions according to the invention generally exhibit more isotropic shrinkage as compared to this known nucleating agent. In other words, to the extent that articles made from the thermoplastic polymer compositions according to the invention shrink upon cooling, the shrinkage exhibited by these articles tends to be more uniform or more even as compared to articles made from thermoplastic polymer compositions containing CaHHPA. This improved isotropy, with less deviation from the desired 1.0 value, typically indicates that parts produced using the thermoplastic polymer composition will exhibit less post-molding deformation and/or warping.

EXAMPLE 12

This example demonstrates some of the physical properties exhibited by a high density polyethylene polymer that has been nucleated with a nucleating agent according to the invention. Three polymer compositions (i.e., Samples 12A, 12B, and 12C) were prepared by respectively compounding 500 ppm, 1,000 ppm, and 2,000 ppm of zinc mandelate into a commercially-available, high density polyethylene polymer having a density of approximately 0.952 g/cm³ and a melt flow index of approximately 19 dg/minute. The polymer compositions were then injection molded into containers on a 300 ton Netstal injection molding machine. For purposes of comparison, containers were also molded using the same commercially-available, high density polyethylene polymer without a nucleating agent being added (Comparative Sample 12). The optical properties of the containers were then measured at the container sidewalls, and the flexural and impact properties were measured using samples drawn from the bottom portion of the containers. The stiffness-impact balance of the samples was calculated by multiplying the flexural modulus (expressed in MPa) and the Gardner impact resistant (expressed in J). The standard deviation of the stiffness-impact balance was calculated using the following equation $$\left(\frac{\sigma_{S/I}}{S/I}\right)^2 = \left(\frac{\sigma_{flex}}{flex}\right)^2 + \left(\frac{\sigma_{impact}}{impact}\right)^2.$$

The values obtained for the samples are reported in Tables 2-5 below.

TABLE 2

Flexural modulus of Samples 12A-12C and Comparative Sample 12.

| Sample | Loading (ppm) | Flexural Modulus (MPa) | Standard Deviation (MPa) |
|---|---|---|---|
| Comparative 12 | — | 1115 | 11 |
| 12A | 500 | 1165 | 5 |
| 12B | 1,000 | 1191 | 7 |
| 12C | 2,000 | 1213 | 5 |

TABLE 3

Gardner impact resistance of Samples 12A-12C and Comparative Sample 12.

| Sample | Loading (ppm) | Gardner Impact Resistance (J) | Standard Deviation (J) |
|---|---|---|---|
| Comparative 12 | — | 12 | 0.39 |
| 12A | 500 | 12.5 | 0.42 |
| 12B | 1,000 | 11.9 | 0.21 |
| 12C | 2,000 | 12 | 0.34 |

TABLE 4

Stiffness-impact balance of Samples 12A-12C and Comparative Sample 12.

| Sample | Loading (ppm) | Stiffness-impact Balance (MPa * J) | Standard Deviation (MPa * J) |
|---|---|---|---|
| Comparative 12 | — | 13715 | 455.4 |
| 12A | 500 | 14563 | 493.3 |
| 12B | 1,000 | 14173 | 263.6 |
| 12C | 2,000 | 14556 | 416.8 |

TABLE 5

Optical properties of Samples 12A-12C and Comparative Sample 12.

| Sample | Loading (ppm) | 1 mm Thickness | | 1.5 mm Thickness | |
|---|---|---|---|---|---|
| | | Haze (%) | Clarity (%) | Haze (%) | Clarity (%) |
| Comparative 12 | — | 100.0 | 34.8 | 100.0 | 2.9 |
| 12A | 500 | 91.5 | 94.7 | 98.6 | 89.1 |
| 12B | 1,000 | 85.0 | 97.2 | 94.3 | 95.6 |
| 12C | 2,000 | 83.0 | 97.8 | 93.2 | 96.8 |

EXAMPLE 13

This example demonstrates some of the physical properties exhibited by a linear low density polyethylene polymer that has been nucleated with a nucleating agent according to the invention. Three polymer compositions (i.e., Samples 13A, 13B, and 13C) were prepared by respectively compounding 500 ppm, 1,000 ppm, and 2,000 ppm of zinc mandelate into a commercially-available, linear low density polyethylene polymer having a density of approximately 0.917 g/cm³ and a melt flow index of approximately 24 dg/minute. The polymer compositions were then injection molded into containers on a 300 ton Netstal injection molding machine. For purposes of comparison, containers were also molded using the same commercially-available, high density polyethylene polymer without a nucleating agent being added (Comparative Sample 13). The optical properties of the containers were then measured at the container sidewalls, and the flexural and impact properties were measured using samples drawn from the bottom portion of the containers. The stiffness-impact balance of the samples and the standard deviation of the stiffness-impact balance were calculated as described above in Example 12. The values obtained for the samples are reported in Tables 6-9 below.

TABLE 6

Flexural modulus of Samples 13A-13C and Comparative Sample 13.

| Sample | Loading (ppm) | Flexural Modulus (MPa) | Standard Deviation (MPa) |
|---|---|---|---|
| C. S. 13 | — | 266 | 1 |
| 13A | 500 | 283 | 1 |
| 13B | 1,000 | 313 | 1 |
| 13C | 2,000 | 323 | 3 |

TABLE 7

Gardner impact resistance of Samples 13A-13C and Comparative Sample 13.

| Sample | Loading (ppm) | Gardner Impact Resistance (J) | Standard Deviation (J) |
|---|---|---|---|
| C. S. 13 | — | 6 | 0.43 |
| 13A | 500 | 6 | 0.29 |
| 13B | 1,000 | 6.2 | 0.29 |
| 13C | 2,000 | 9 | 0.12 |

TABLE 8

Stiffness-impact balance of Samples 13A-13C and Comparative Sample 13.

| Sample | Loading (ppm) | Stiffness-impact Balance (MPa * J) | Standard Deviation (MPa * J) |
|---|---|---|---|
| C. S. 13 | — | 1543 | 114.5 |
| 13A | 500 | 1698 | 82.3 |
| 13B | 1,000 | 1941 | 91.0 |
| 13C | 2,000 | 2907 | 47.2 |

TABLE 9

Optical properties of Samples 13A-13C and Comparative Sample 13.

| | | 1 mm Thickness | | 1.5 mm Thickness | |
|---|---|---|---|---|---|
| Sample | Loading (ppm) | Haze (%) | Clarity (%) | Haze (%) | Clarity (%) |
| C. S. 13 | — | 79.7 | 95.4 | 71.7 | 11.8 |
| 13A | 500 | 86.3 | 98.7 | 89.5 | 58.0 |
| 13B | 1,000 | 78.6 | 93.7 | 96.8 | 94.2 |
| 13C | 2,000 | 71.3 | 84.7 | 97.7 | 97.5 |

EXAMPLE 14

This example demonstrates some of the physical properties exhibited by a linear low density polyethylene polymer that has been nucleated with a nucleating agent according to the invention. Two polymer compositions (i.e., Samples 14A and 14B) were prepared by respectively compounding 500 ppm and 1,000 ppm of zinc mandelate into a commercially-available, linear low density polyethylene polymer having a density of approximately 0.918 g/cm$^3$ and a melt flow index of approximately 1 dg/minute. For purposes of comparison, a third polymer composition (i.e., Comparative Sample 14Y) was prepared by compounding approximately 1,000 ppm of HYPERFORM® 20E (available from Milliken & Company) into the same linear low density polyethylene polymer. The polymer compositions were then used to produce blown films on a Future Design film line with the following setup: 4 inch die, 2.0 mm die gap, BUR 2.5, DDR 21, and output 29 kg/h. For purposes of comparison, blown film (i.e., Comparative Sample 14X) was also produced using the virgin linear low density polyethylene polymer (i.e., the polymer without any nucleating agent). The tear strength, dart drop impact, Young's modulus, and haze of the resulting films were measured and are reported in Tables 10-13.

TABLE 10

Tear strength of Samples 14A and 14B and Comparative Samples 14X and 14Y.

| | | Machine Direction | | Transverse Direction | |
|---|---|---|---|---|---|
| Sample | Loading (ppm) | Tear Strength (g) | Standard Deviation (g) | Tear Strength (g) | Standard Deviation (g) |
| C. S. 14X | — | 705.6 | 90.7 | 997.1 | 52.7 |
| C. S. 14Y | 1,000 | 617.0 | 46.9 | 981.8 | 78.2 |
| 14A | 500 | 819.2 | 28.9 | 1002.2 | 39.6 |
| 14B | 1,000 | 876.8 | 50.9 | 1030.4 | 37.6 |

TABLE 11

Dart drop impact of Samples 14A and 14B and Comparative Samples 14X and 14Y.

| Sample | Loading (ppm) | Dart Drop Impact (g) | Standard Deviation (g) |
|---|---|---|---|
| C. S. 14X | — | 225.5 | 1.2 |
| C. S. 14Y | 1,000 | 227.0 | 1.5 |
| 14A | 500 | 273.5 | 1.1 |
| 14B | 1,000 | 309.5 | 1.6 |

TABLE 12

Young's modulus of Samples 14A and 14B and Comparative Samples 14X and 14Y.

| | | Machine Direction | | Transverse Direction | |
|---|---|---|---|---|---|
| Sample | Loading (ppm) | Young's Modulus (MPa) | Standard Deviation (MPa) | Young's Modulus (MPa) | Standard Deviation (MPa) |
| C. S. 14X | — | 151.2 | 14.5 | 218.5 | 25.1 |
| C. S. 14Y | 1,000 | 166.1 | 17.2 | 234.3 | 19.5 |
| 14A | 500 | 148.2 | 4.3 | 173.9 | 15.1 |
| 14B | 1,000 | 147.1 | 8.0 | 162.3 | 15.6 |

TABLE 13

Haze of Samples 14A and 14B and Comparative Samples 14X and 14Y.

| Sample | Loading (ppm) | Haze (%) | Standard Deviation (%) |
|---|---|---|---|
| C. S. 14X | — | 18.1 | 0.7 |
| C. S. 14Y | 1,000 | 10.2 | 0.2 |
| 14A | 500 | 19.8 | 0.6 |
| 14B | 1,000 | 18.0 | 0.8 |

EXAMPLE 15

This example demonstrates some of the physical properties exhibited by a high density polyethylene polymer that has been nucleated with a nucleating agent according to the invention. A polymer composition (i.e., Sample 15A) was prepared by compounding approximately 2,000 ppm of zinc mandelate into a commercially-available, high density polyethylene polymer having a density of approximately 0.962 g/cm$^3$ and a melt flow index of approximately 0.9 dg/minute. For purposes of comparison, a second polymer composition (i.e., Comparative Sample 15Y) was prepared by compounding approximately 2,000 ppm of HYPERFORM® 20E (available from Milliken & Company) into the same high density polyethylene polymer. The polymer compositions were then used to produce blown films on a Future Design film line with the following setup: 4 inch die, 2.0 mm die gap, BUR 2.3, DDR 21, and output 29 kg/h. For purposes of comparison, blown film (i.e., Comparative Sample 15X) was also produced using the virgin high density polyethylene polymer (i.e., the polymer without any nucleating agent). The dart drop impact of the resulting films was measured and is reported in Table 14.

TABLE 14

Dart drop impact of Samples 15A and Comparative Samples 15X and 15Y.

| Sample | Loading (ppm) | Dart Drop Impact (g) | Standard Deviation (g) |
| --- | --- | --- | --- |
| C. S. 15X | — | 59.0 | 1.1 |
| C. S. 15Y | 2,000 | n.d. | 1.3 |
| 15A | 2,000 | 68.0 | 1.1 |

The dart drop impact of Comparative Sample 15Y proved to be too low to determine using the test method. Accordingly, the value for Comparative Sample 15Y is reported as "n.d."

EXAMPLE 16

This example demonstrates some of the physical properties exhibited by a high density polyethylene polymer that has been nucleated with a nucleating agent according to the invention. A polymer composition (i.e., Sample 16A) was prepared by compounding approximately 3 wt. % of zinc mandelate into a commercially-available, high density polyethylene polymer having a density of approximately 0.952 g/cm³ and a melt flow index of approximately 19 dg/minute. For purposes of comparison, a second polymer composition (i.e., Comparative Sample 16Y) was prepared by compounding approximately 3 wt. % of HYPERFORM® 20E (available from Milliken & Company) into the same high density polyethylene polymer. The polymer compositions were then let down at a ratio of approximately 3% into another commercially-available high density polymer having a density of approximately 0.953 g/cm³ and a melt flow index of approximately 6 dg/minute and the resulting polymer blends were injection molded. The resulting parts were then tested to determine their multi-axial impact at temperatures of 23° C. and −30° C., tensile strength at yield, flexural chord modulus, shrinkage in the machine direction (i.e., with flow), and shrinkage in the transverse direction (i.e., cross flow). The measured values for each sample and the virgin high density polyethylene polymer (Comparative Sample 16X) are reported in Table 15 below.

TABLE 15

Select physical properties of Sample 16A and Comparative Samples 16X and 16Y.

| Property | C. S. 16X | C. S. 16Y | 16A |
| --- | --- | --- | --- |
| Multi-Axial Impact (2.2 m/s at 23° C.) | 17.99 J<br>5 Ductile | 17.00 J<br>5 Ductile | 17.55 J<br>5 Ductile |
| Multi-Axial Impact (2.2 m/s at −30° C.) | 21.24 J<br>5 Ductile | 20.49 J<br>5 Ductile | 20.69 J<br>5 Ductile |
| Tensile Strength at Yield | 3,161 psi<br>(21.79 MPa) | 3,445 psi<br>(23.75 MPa) | 3,197 psi<br>(22.04 MPa) |
| Flexural Chord Modulus | 136,877 psi<br>(943.734 MPa) | 129,682 psi<br>(894.126 MPa) | 133,504 psi<br>(920.478 MPa) |
| M.D. Shrinkage | 2.69% | 2.35% | 1.68% |
| T.D. Shrinkage | 2.71% | 1.81% | 2.59% |

EXAMPLE 17

This example demonstrates some of the physical properties exhibited by a high density polyethylene polymer that has been nucleated with a nucleating agent according to the invention. A polymer composition (i.e., Sample 17A) was prepared by compounding approximately 3 wt. % of zinc mandelate into a commercially-available, high density polyethylene polymer having a density of approximately 0.952 g/cm³ and a melt flow index of approximately 19 dg/minute. For purposes of comparison, a second polymer composition (i.e., Comparative Sample 17Y) was prepared by compounding approximately 3 wt. % of HYPERFORM® 20E (available from Milliken & Company) into the same high density polyethylene polymer. The polymer compositions were then let down at a ratio of approximately 3% into another commercially-available high density polymer having a melt flow index of approximately 35 dg/minute and the resulting polymer blends were injection molded. The resulting parts were then tested to determine their multi-axial impact at temperatures of 23° C. and −30° C., tensile strength at yield, flexural chord modulus, shrinkage in the machine direction (i.e., with flow), and shrinkage in the transverse direction (i.e., cross flow). The measured values for each sample and the virgin high density polyethylene polymer (Comparative Sample 17X) are reported in Table 15 below.

TABLE 16

Select physical properties of Sample 17A and Comparative Samples 17X and 17Y.

| Property | C. S. 17X | C. S. 17Y | 17A |
| --- | --- | --- | --- |
| Multi-Axial Impact (2.2 m/s at 23° C.) | 6.31 J<br>5 Brittle | 15.55 J<br>5 Ductile | 14.38 J<br>5 Ductile |
| Multi-Axial Impact (2.2 m/s at −30° C.) | 7.86 J<br>5 Brittle | 19.79 J<br>5 Ductile | 20.16 J<br>5 Ductile |
| Tensile Strength at Yield | 3,005 psi<br>(20.72 MPa) | 3,466 psi<br>(23.90 MPa) | 3,502<br>(24.15 MPa) |
| Flexural Chord Modulus | 119,517 psi<br>(824.041 MPa) | 131,205 psi<br>(904.627 MPa) | 143,209 psi<br>(987.391 MPa) |
| M.D. Shrinkage | 2.48% | 1.8% | 2.16% |
| T.D. Shrinkage | 2.38% | 1.72% | 2.73% |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the subject matter of this application (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the subject matter of the application and does not pose a limitation on the scope of the subject matter unless otherwise claimed. No language in the specification should be construed as indicating any non-claimed element as essential to the practice of the subject matter described herein.

Preferred embodiments of the subject matter of this application are described herein, including the best mode known to the inventors for carrying out the claimed subject matter. Variations of those preferred embodiments may become apparent to those of ordinary skill in the art upon reading the foregoing description. The inventors expect skilled artisans to employ such variations as appropriate, and the inventors intend for the subject matter described herein to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the present disclosure unless otherwise indicated herein or otherwise clearly contradicted by context.

What is claimed is:

1. A thermoplastic polymer composition consisting of:
   (a) a thermoplastic polymer, wherein the thermoplastic polymer is a polyethylene; and
   (b) a nucleating agent, the nucleating agent comprising a compound conforming to the structure of Formula (I)

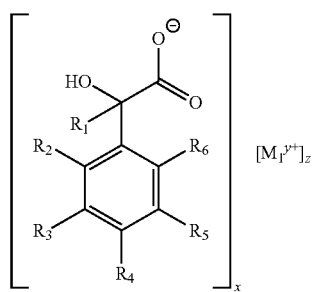

(I)

wherein x is a positive integer; $R_1$, $R_2$, $R_3$, $R_4$, $R_5$, and $R_6$ are hydrogen; each $M_1$ is a metal cation selected from the group consisting of zinc cations; y is the valence of the metal cation; z is a positive integer;
   wherein the values of x, y, and z satisfy the equation x=yz; and
   (c) optionally, one or more additional components selected from the group consisting of additional thermoplastic polymers, antioxidants, anti-blocking agents, fillers, reinforcing agents, nucleating agents, clarifying agents, acid scavengers, polymer processing additives, polymer cross-linking agents, slip agents, and fatty acid ester compounds.

2. The thermoplastic polymer composition of claim 1, wherein the nucleating agent is present in the thermoplastic polymer composition in an amount of about 100 to about 5,000 parts-per-million (ppm), based on the total weight of the thermoplastic polymer composition.

3. The thermoplastic polymer composition of claim 1, wherein the compound is a racemate.

4. The thermoplastic polymer composition of claim 1, wherein the thermoplastic polymer is a high density polyethylene.

5. The thermoplastic polymer composition of claim 1, wherein the thermoplastic polymer is a medium density polyethylene.

6. The thermoplastic polymer composition of claim 1, wherein the nucleating agent is present in the thermoplastic polymer composition in an amount of about 250 ppm or more, based on the total weight of the thermoplastic polymer composition.

7. The thermoplastic polymer composition of claim 1, wherein the nucleating agent is present in the thermoplastic polymer composition in an amount of about 500 ppm or more, based on the total weight of the thermoplastic polymer composition.

* * * * *